(12) United States Patent
Lin et al.

(10) Patent No.: US 7,776,863 B2
(45) Date of Patent: Aug. 17, 2010

(54) METHODS OF TREATING HIV INFECTION

(75) Inventors: Pin-Fang Lin, Branford, CT (US); Beata Nowicka-Sans, Newington, CT (US); Gregory Yamanaka, Middletown, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1203 days.

(21) Appl. No.: 11/064,683

(22) Filed: Feb. 24, 2005

(65) Prior Publication Data
US 2005/0215545 A1    Sep. 29, 2005

Related U.S. Application Data

(60) Provisional application No. 60/555,767, filed on Mar. 24, 2004.

(51) Int. Cl.
| | |
|---|---|
| A61K 31/497 | (2006.01) |
| A61K 31/50 | (2006.01) |
| A61K 31/33 | (2006.01) |
| A61K 31/52 | (2006.01) |
| A61K 31/215 | (2006.01) |
| A61K 38/00 | (2006.01) |

(52) U.S. Cl. ............. 514/253.04; 514/241; 514/252.02; 514/252.11; 514/252.01; 514/183; 514/467; 514/530; 514/263.1; 514/2

(58) Field of Classification Search ............ 514/253.04, 514/241, 252.02, 252.11, 252, 183, 467, 514/530, 263.1, 2
See application file for complete search history.

(56) References Cited

U.S. PATENT DOCUMENTS

| 6,172,110 B1 * | 1/2001 | Lee et al. .................... 514/530 |
| 6,476,034 B2 | 11/2002 | Wang et al. |
| 6,632,819 B1 | 10/2003 | Wang et al. |
| 6,777,440 B2 * | 8/2004 | Walker et al. ............... 514/467 |
| 7,501,420 B2 * | 3/2009 | Wang et al. ............ 514/253.04 |
| 2003/0207910 A1 * | 11/2003 | Wang et al. ................. 514/300 |
| 2003/0220341 A1 * | 11/2003 | Bridger et al. .............. 514/249 |

FOREIGN PATENT DOCUMENTS

WO    WO 2004/014380 A    2/2004

OTHER PUBLICATIONS

Clercq et al. "Highly potent and selective inhibition of Human Immunodeficiency virus by Bicyclam derivative JM3100," Antimicrobial Agents and Chemotherapy, 1994, vol. 38, No. 4, pp. 668-674.*
Hammer et al. "Issue in combination antiretroviral therapy: A Review," J. Acquired Immune Deficiency Syndromes, 1994, vol. 7, Suppl 2, S24-S37.*
Jordan et al. "Systematic review and meta-analysis of evidence for increasing number of drugs in antiviral combination therapy," BMJ 2002, vol. 324, pp. 1-10.*
Vippaguanta et al. "Crystalline Solids," Advanced Drug Delivery Reviews, 2001, vol. 48, pp. 3-26.*
West "Solid state chemistry and its application," John Wiley & Sons, 1988, New York, p. 365.*
Kirk—othmer Encyclopedia of Chemical technology, John Wiley & Sons 2002, chapter 4, Crystal Characteristics.*
Lin, P.-F., "Characterization of HIV-1 Variants Resistant to BMS-806, a Novel HIV-1 Entry Inhibitor," XIth Int. HIV Drug Resistance Workshop, Seville, Spain, Jul. 2002.
Lin, P.-F. et al, "Identification and Characterization of a Novel Inhibitor of HIV-1 Entry I: Virology and Resistance," 9th Conference on Retroviruses and Opportunistic Infections, Seattle, WA, Feb. 22-28, 2002.
Lin, P.-F. et al, "Identification and Characterization of a Novel Inhibitor of HIV-1 Entry II: Mechanism of Action," 9th Conference on Retroviruses and Opportunistic Infections, Seattle, WA, Feb. 22-28, 2002.
Lin, P.-F. et al, "A small molecule HIV-1 inhibitor that targets the HIV-1 envelope and inhibits CD4 receptor binding," Proc. Nat. Acad. Sci. USA 2003, 100(19), 11013-11018.
Wang, T. et al, "Discovery of 4-Benzoyl-1-[(4-methoxy-1H-pyrrolo[2,3-b]pyridin-3-yl)oxoacetyl]-2-(R)-methylpiperazine (BMS-378806): A Novel HIV-1 Attachment Inhibitor That Interferes with CD4-gp120 Interactions," J. Med. Chem. 2003 46, 4236-4239.
Guo, Q. et al, "Biochemical and Genetic Characterizations of a Novel Human Immunodeficiency Virus Type 1 Inhibitor That Blocks gp120-CD4 Interactions," J. Virol. 2003 77(19), 10528-10536.
Kuhmann, S. E. and Moore, J. P., "HIV-1 entry inhibitor entrances," Trends Pharm. Sci. 2004, 25(3), 117-120.
Madani, N. et al, "Localized Changes in the gp120 Envelope Glycoprotein Confer Resistance to Human Immunodeficiency Virus Entry Inhibitors BMS-806 and #155," J. Virol. 2004, 78(7), 3742-3752.

(Continued)

*Primary Examiner*—Shengjun Wang
(74) *Attorney, Agent, or Firm*—John F. Levis

(57) ABSTRACT

The invention encompasses pharmaceutical compositions and methods for using Compound 1 in combination with other agents for treating patients with AIDS or HIV infection.

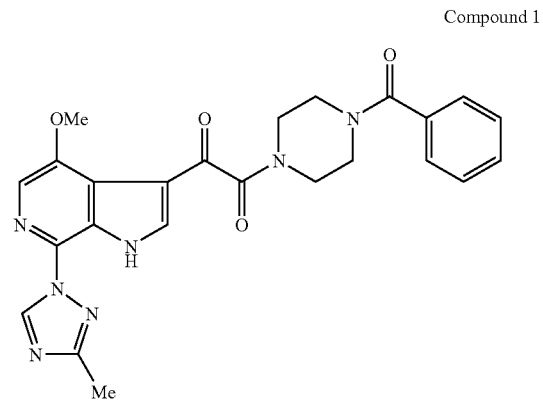

Compound 1

2 Claims, No Drawings

OTHER PUBLICATIONS

Si, Z. et al, "Small-molecule inhibitors of HIV-1 entry block receptor-induced conformational changes in the viral envelope glycoproteins," *Proc. Nat. Acad. Sci USA* 2004, 101(14), 5036-5041.

Moore, P. L. et al, "Predicted genotypic resistance to the novel entry inhibitor, BMS-378806, among HIV-1 isolates of subtypes A to G," *AIDS* 2004, 18(17), 2327-2330.

Wang, H.-G.H. et al, "A Novel Class of HIV-1 Inhibitors that Targets the Viral Envelope and Inhibits CD4 Receptor Binding," *Curr. Pharm. Design* 2004, 10, 1785-1793.

De Clercq, E., "New Approaches toward Anti-HIV Chemotherapy," *J. Med. Chem.* 2005, 48(5), 1297-1313.

Meanwell, N., "The Discovery and Characterization of a Novel Inhibitor of HIV Attachment," Gordon Research Conferences, New London, NH, 2002.

Guo, Q. et al, "Mechanism of a Novel HIV-1 Inhibitor That Targets the Viral Envelope and Inhibits CD4 Binding," 42nd Interscience Conference on Antimicrobial Agents and Chemotherapy, San Diego, CA, Sep. 27-30, 2002.

Ho, H. et al, "Impact of an HIV-1 Attachment Inhibitor on Viral Envelope Gp120," 43rd Interscience Conference on Antimicrobial Agents and Chemotherapy, Chicago, IL, Sep. 14-17, 2003.

Lin, P.-F. et al, "Characterization of a Small Molecule HIV-1 Attachment Inhibitor BMS-488043: Virology, Resistance, and Mechanism of Action," 11th Conference on Retroviruses and Opportunistic Infections, San Francisco, CA, Feb. 8-11, 2004.

Hanna, G. et al, "Safety, Tolerability and Pharmacokinetics (PK) of a Novel, Small Molecule HIV-1 Attachment Inhibitor, BMS-488043, After Single and Multiple Oral Doses in Healthy Subjects," 11th Conference on Retroviruses and Opportunistic Infections, San Francisco, CA, Feb. 8-11, 2004.

Hanna, G. et al, "Antiviral Activity, Safety, and Tolerability of a Novel, Small Molecule HIV-1 Attachment Inhibitor, BMS-488043, in HIV-1-infected Subjects," 11th Conference on Retroviruses and Opportunistic Infections, San Francisco, CA, Feb. 8-11, 2004.

Ho, H. et al, "Effect of an HIV-1 Attachment Inhibitor on the Conformation of the Viral Envelope gp120," 17th International Conference on Antiviral Research, Tucson, AZ, May 2-6, 2004.

Lin, P.-F., "Structural Modulations of Viral Envelope by HIV-1 Attachment Inhibitors," 4th Frederick Workshop on the Cell Biology of Viral Entry, Frederick, MD, May 5, 2004.

Lin, P.-F., "In Vitro Resistance Profile of Small Molecule HIV-1 Attachment Inhibitors," XIII International HIV Drug Resistance Workshop, Tenerif, Spain, Jun. 8-12, 2004.

Lin, P.-F., "Mechanism and Clinical Efficacy of a Novel HIV-1 Attachment Inhibitor," 2004 International Meeting of the Institute of Human Virology, Baltimore, MD, Oct. 11-Nov. 4, 2004.

Ho, H. et al, "Inhibition Mechanism of Small-Molecule HIV-1 Attachment Inhibitors," 12th Conference on Retroviruses and Opportunistic Infections, Boston, MA, Feb. 22-25, 2005.

Lin, P.-F. et al, "In Vitro Resistance Profile of Small Molecule HIV-1 Attachment Inhibitors," 3rd European HIV Drug Resistance Workshop, Athens, Greece, Mar. 30-Apr. 1, 2005.

\* cited by examiner

METHODS OF TREATING HIV INFECTION

CROSS-REFERENCE TO RELATED APPLICATIONS

This application claims the benefit of U.S. provisional application U.S. Ser. No. 60/555,767, filed Mar. 24, 2004.

BACKGROUND OF THE INVENTION

HIV-1 (human immunodeficiency virus-1) infection remains a major medical problem, with an estimated 42 million people infected worldwide at the end of 2002. The number of cases of HIV and AIDS (acquired immunodeficiency syndrome) has risen rapidly. In 2002, approximately 5 million new infections were reported and 3.1 million people died from AIDS. Currently available drugs for the treatment of HIV include ten nucleoside reverse transcriptase (RT) inhibitors or approved single pill combinations: zidovudine or AZT (or Retrovir®), didanosine or DDI (or Videx®), stavudine or D4T (or Zerit®), lamivudine or 3TC (or Epivir®), zalcitabine or DDC (or Hivid®), abacavir succinate (or Ziagen®), tenofovir disoproxil fumarate salt (or Viread®), emtricitabine (or Emtriva®), Combivir® (contains 3TC and AZT), Trizivir® (contains abacavir, 3TC and AZT); three non-nucleoside reverse transcriptase inhibitors: nevirapine (or Viramune®), delavirdine (or Rescriptor®) and efavirenz (or Sustiva®), eight peptidomimetic protease inhibitors or approved formulations: saquinavir (or Invirase® or Fortovase®), indinavir (or Crixivan®), ritonavir (or Norvir®), nelfinavir (or Viracept®), amprenavir (or Agenerase®), atazanavir (Reyataz®), fosamprenavir (or Lexiva), Kaletra® (contains lopinavir and ritonavir), and one fusion inhibitor enfuvirtide (or T-20 or Fuzeon®).

Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. Despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present (Larder and Kemp; Gulick; Kuritzkes; Morris-Jones et al; Schinazi et al; Vacca and Condra; Flexner; Berkhout and Ren et al; (Ref. 6-14)). Thus, there is continuing need for new compounds and methods of treatment for HIV infection.

1-Benzoyl-4-[2-[4-methoxy-7-(3-methyl-1H-1,2,4-triazol-1-yl)-1H-pyrrolo[2,3-c]pyridin-3-yl]-1,2-dioxoethyl]-piperazine (Compound 1) is an HIV-1 attachment inhibitor demonstrating potent antiviral activity against a variety of laboratory and clinical strains of HIV-1 (see U.S. patent application U.S. 2003 0207910, published Nov. 6, 2003).

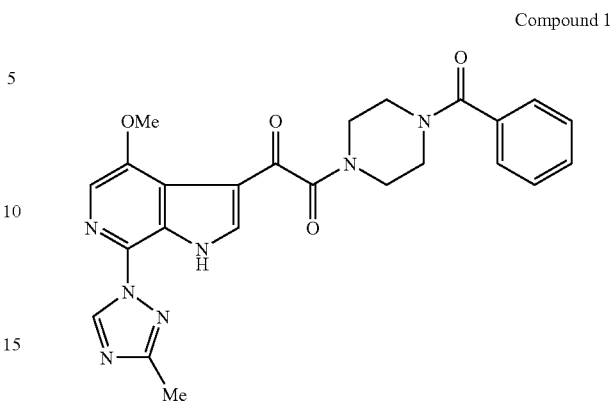

Compound 1

Compound 1 acts by selectively preventing attachment of the exterior viral envelope protein gp120 to its cellular receptor CD4. Binding of gp120 to CD4 is the first step in viral entry and is distinct from the subsequent interaction with a chemokine receptor (CCR5 or CXCR4) or virus-cell fusion event. By inhibiting this interaction, Compound 1 blocks viral entrance into cells.

DESCRIPTION OF THE INVENTION

The invention encompasses pharmaceutical compositions and methods for treating HIV infection and AIDS.

One aspect of the invention is a method for treating HIV infection in a human patient comprising the administration of a therapeutically effective amount of 1-benzoyl-4-[2-[4-methoxy-7-(3-methyl-1H-1,2,4-triazol-1-yl)-1H-pyrrolo[2,3-c]pyridin-3-yl]-1,2-dioxoethyl]-piperazine (Compound 1), or a pharmaceutically acceptable salt or solvate thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt or solvate thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable salt or solvate thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt or solvate thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt or solvate thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt or solvate thereof.

Another aspect of the invention is a method wherein the agent is a CXCR4 inhibitor.

Another aspect of the invention is a method wherein the CXCR4 inhibitor is AMD-3100, or a pharmaceutically acceptable salt or solvate thereof.

Another aspect of the invention is a method wherein the agent is an HIV budding or maturation inhibitor.

Another aspect of the invention is a method wherein the budding or maturation inhibitor is PA-457, or a pharmaceutically acceptable salt or solvate thereof.

Another aspect of the invention is a method wherein the agent is an HIV integrase inhibitor.

Another aspect of the invention is a method wherein the HIV integrase inhibitor is 3-[(4-fluorobenzyl)methoxycarbamoyl]-2-hydroxyacrylic acid or 2-(2,2)-dimethyl-5-oxo-[1,3]-dioxolan-4-ylidene)-N-(4-fluorobenzyl)-N-methoxyacetamide, or a salt or solvate thereof.

Another aspect of the invention is a pharmaceutical composition comprising a therapeutically effective amount of 1-benzoyl-4-[2-[4-methoxy-7-(3-methyl-1H-1,2,4-triazol-1-yl)-1H-pyrrolo[2,3-c]pyridin-3-yl]-1,2-dioxoethyl]-piperazine, or a pharmaceutically acceptable salt or solvate thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt or solvate thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt or solvate thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt or solvate thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt or solvate thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt or solvate thereof.

Another aspect of the invention is a method wherein the agent is a CXCR4 inhibitor.

Another aspect of the invention is a method wherein the CXCR4 inhibitor is AMD-3100, or a pharmaceutically acceptable salt or solvate thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt or solvate thereof.

Another aspect of the invention is the composition wherein the agent is an HIV integrase inhibitor.

Another aspect of the invention is the composition wherein the HIV integrase inhibitor is 3-[(4-fluorobenzyl)methoxycarbamoyl]-2-hydroxyacrylic acid or 2-(2,2)-dimethyl-5-oxo-[1,3]-dioxolan-4-ylidene)-N-(4-fluorobenzyl)-N-methoxyacetamide, or a pharmaceutically acceptable salt or solvate thereof.

"Combination," "coadministration," "concurrent," and similar terms referring to the administration of Compound 1 with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The invention includes all pharmaceutically acceptable salt forms of Compound 1. Pharmaceutically acceptable salts are those in which the counter ions do not contribute significantly to the physiological activity or toxicity of the compounds and as such function as pharmacological equivalents. In many instances, salts have physical properties that make them desirable for formulation, such as solubility or crystallinity. The salts can be made according to common organic techniques employing commercially available reagents. Suitable anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate.

The invention also includes all solvated forms of Compound 1, particularly hydrates. Solvates do not contribute significantly to the physiological activity or toxicity of the compounds and as such function as pharmacological equivalents. Solvates may form in stoichiometric amounts or may form from adventitious solvent or a combination of both. One type of solvate is hydrate. Some hydrated forms include monohydrate, hemihydrate, and dihydrate.

Biological Methods

Compound 1 demonstrated synergistic or additive-synergistic HIV antiviral activity when used in conjunction with a variety of other antiviral agents, as described below.

Virus and cell lines. The T-cell lines, MT-2 and PM-1 were obtained through the AIDS Research and Reference Reagent Program, NIAID, and were contributed by Dr. D. Richman and Dr. R. Gallo, respectively. Both cell lines were cultured in RPMI 1640 medium supplemented with 10% fetal bovine serum, 2 mM L-glutamine and sub-cultured twice a week. The LAI strain of HIV-1 was obtained from the Fred Hutchinson Cancer Research Center, and the Bal strain was from NIH. Both virus stocks were amplified and titered in MT-2 cells (LAI) and PM-1 cells (Bal) using a virus infectivity assay.

Chemicals. Compound 1, atazanavir, didanosine, stavudine, efavirenz, enfuvirtide (T-20), T-1249, AMD-3100, Sch-C, Sch-D and UK-427,857 were synthesized using published or known reactions. Amprenavir, indinavir, nelfinavir, nevirapine, lopinavir, lamivudine, ritonavir, tenofovir, saquinavir, delavirdine and abacavir were extracted from commercial formulations of the prescribed drugs and purified using published or common techniques. Tenofovir was tested as tenovir disopoxil fumerate. Zalcitabine was obtained from the National Institutes of Health. Zidovudine was purchased from Sigma and emtricitabine from Moravek Biochemicals. 3-[(4-Fluorobenzyl)methoxycarbamoyl]-2-hydroxyacrylic acid (Compound 2) and 2-(2,2)-dimethyl-5-oxo-[1,3]-dioxolan-4-ylidene)-N-(4-fluorobenzyl)-N-methoxyacetamide (Compound 3) are described in U.S. Pat. No. 6,777,440. Purities of the anti-HIV agents were greater than 95% except for AMD-3100 (>90%), Sch-D (80%), and UK-427,857 (>90%).

Drug Susceptibility and Cytotoxicity Assays. For drug susceptibility assays, MT-2 cells were infected with HIV-1 LAI (or PM-1 cells with HIV-1 Bal) at an MOI of 0.005, and seeded into 96-well microtiter plates ($0.1 \times 10^6$ cells/ml) containing serial dilutions of test compounds. The drug combinations were set up using ratios of the two drugs of 1:1, 1:2.5 and 2.5:1 times the $EC_{50}$ value determined for each drug in prior multiple experiments. Each drug ratio consisted of an array of 3-fold serial dilutions, and was performed in quadruplicate. The plates were incubated at 37° C./5% $CO_2$. The MT-2 cells infected with HIV-1 LAI were incubated for 5 days. On day-five post-infection, 20 µl from each well was harvested and quantitated by a reverse transcriptase (RT) assay, or in samples involving non-nucleoside RT inhibitors, an MTS assay. The PM-1 cells infected with HIV-1 Bal and used for studying the combinations with CCR5 inhibitors were incubated for six days. On day-six post-infection, 20 µl from each well was harvested, 20- and 50-fold diluted and quantitated by p24 assay. Cytotoxicity assays were performed using uninfected cells, exposed to the same drug combinations, and incubated for six days. Cell viability was determined by an MTS assay. The $CC_{50}$ values were calculated by using the exponential form of the median effect equation as mentioned below for calculation of $EC_{50}$.

Analysis of Drug Combination Effects. For determination of CI values, drugs were diluted in a fixed ratio and multiple ratios were analyzed. The drug serial dilutions spanned a range of concentrations near the $EC_{50}$ value of each compound, so that equivalent antiviral activities could be compared. Concentration-response curves were estimated for each individual drug and every combination using the median-effect equation. The equation was fit using a nonlinear regression routine (Proc Nlin) in PC SAS version 8.01 (SAS Institute Inc., SAS Version 8.01, Cary, N.C.: SAS Institute Inc., 1990).

$EC_{50}$ values for each drug were determined from the single drug experiments, using the median effect equation, $Fa=1/[1+(ED_{50}/\text{drug concentration})^m]$. In this equation, Fa stands for "fraction affected," and represents the fraction of the viral load that has been inactivated. For example, Fa of 0.75 indicates that viral replication had been inhibited by 75%, relative to the no-drug controls. $ED_{50}$ is drug concentration that is expected to reduce the amount of virus by 50%, and m is a parameter that reflects the slope of the concentration-response curve.

To assess antiviral effects of different drug combination treatments, combination indices (CIs) were calculated according to Chou and Rideout. The combination index was computed as $$CI = [D]_{1/[Dm]1} + [D]_{2/[Dm]2}$$

In this equation [Dm]1 and [Dm]2 are the concentrations of drugs that would individually produce a specific level of effect, while [D]1 and [D]2 are the concentrations of drugs in combination that would produce the same level of effect.

Theoretically, additivity is implied if the CI is equal to one, synergy if the CI is less than one, and antagonism if the CI is greater than one. However, extensive experience with combination studies indicates that there are inherent laboratory variables that must be taken into account in interpreting the CIs. At best, we can construct a range that contains the likely values for the CI, given the noise in the data. In this report, these ranges are reported in parentheses next to each point estimate of the CI. For example, when we report a CI of "0.53 (0.46, 0.60)" this means that our best estimate of the CI is 0.53, but due to noise in the data, values from 0.46 to 0.60 are also reasonable values for the CI. This range, 0.46 to 0.60 falls entirely below the value of 1.0, and hence all likely values for the CI are less than 1.0. Therefore, we can infer synergistic behavior for this case. If the range fell entirely above 1.0, we would infer antagonistic behavior. If the range were to include 1.0, we would infer additivity.

In carrying out the combination experiments below, the $EC_{50}$ for Compound 1 and each comparator compound was determined during the course of each study, and used in the subsequent data analysis. The determined values are consistent with our previously published data and are shown in Table 1.

TABLE 1

Anti-HIV Activity of the Compounds Used in Two-Drug Combination Studies.

| Compound | $EC_{50}$ (µM) | Highest Concentration Used (µM) |
|---|---|---|
| Compound 1 | 0.0001-0.0003 | 0.15 |
| Abacavir | 0.326 | 90 |
| Tenofovir | 0.008 | 6.0 |
| Zalcitabine | 0.034 | 15 |
| Didanosine | 0.652 | 300 |
| Stavudine | 0.072 | 90 |
| Zidovudine | 0.001 | 0.9 |
| Lamivudine | 0.030 | 12 |
| Emtricitabine | 0.025 | 30 |
| Efavirenz | 0.001 | 0.15 |
| Nevirapine | 0.107 | 9.0 |
| Delavirdine | 0.025 | 0.5 |
| Indinavir | 0.003 | 3.0 |
| Atazanavir | 0.0007 | 0.15 |
| Lopinavir | 0.004 | 3.0 |
| Nelfinavir | 0.003 | 0.9 |
| Amprenavir | 0.011 | 3.0 |
| Saquinavir | 0.005 | 3.0 |

TABLE 1-continued

Anti-HIV Activity of the Compounds Used in Two-Drug Combination Studies.

| Compound | $EC_{50}$ (µM) | Highest Concentration Used (µM) |
|---|---|---|
| Ritonavir | 0.007 | 3.0 |
| Enfuvirtide | 0.001 | 0.9 |
| T-1249 | | |
| AMD-3100 | 0.005 | 0.8 |
| SchC | 0.0009 | 0.9 |
| SchD | | |
| UK-427,857 | | |
| Compound 2 | 0.079 | 4.0 |

Two-Drug Combinations of Compound 1 with Nucleoside Reverse Transcriptase Inhibitors. Nucleoside RT inhibitors were combined with Compound 1 at a range of concentrations near the $EC_{50}$ value of each compound, so that equivalent antiviral activities could be compared. All estimates were computed using SAS Proc NLIN, and a two-parameter logistic. Data is presented in Table 2 as the combination indices and the asymptotic confidence intervals for RT inhibitors at different molar ratios (see Materials and Methods). Nucleoside RT inhibitors show synergistic to additive-synergistic antiviral effects in combination with Compound 1. No significant antagonism of anti-HIV activity is observed. No enhanced cytotoxicity was encountered at the highest concentrations tested with any of the drug combinations, as measured by MTS reduction assay.

TABLE 2

Two-Drug Combinations using Compound 1 and Nucleoside Reverse Transcriptase Inhibitors.

| Molar Ratio ($EC_{50}$ Ratio)[a] | Combination Indices at % HIV Inhibition[b] (Confidence Interval) | | | Overall Result |
|---|---|---|---|---|
| | 50% | 75% | 90% | |
| *Zalcitabine* | | | | |
| 1:100 (1:1) | 0.58 (0.46, 0.69) | 0.61 (0.43, 0.78) | 0.69 (0.39, 1.00) | Synergistic |
| 1:250 (1:2.5) | 0.55 (0.47, 0.63) | 0.56 (0.44, 0.68) | 0.65 (0.43, 0.86) | |
| 1:40 (2.5:1) | 0.24 (0.22, 0.26) | 0.18 (0.16, 0.20) | 0.14 (0.12, 0.17) | |
| *Emtricitabine* | | | | |
| 1:200 (1:1) | 0.42 (0.35, 0.50) | 0.49 (0.37, 0.61) | 0.60 (0.38, 0.83) | Synergistic |
| 1:500 (1:2.5) | 0.19 (0.15, 0.22) | 0.35 (0.26, 0.44) | 0.67 (0.36, 0.99) | |
| 1:80 (2.5:1) | 0.11 (0.09, 0.12) | 0.26 (0.21, 0.31) | 0.67 (0.44, 0.89) | |
| *Didanosine* | | | | |
| 1:2000 (1:1) | 0.31 (0.29, 0.32) | 0.16 (0.15, 0.17) | 0.08 (0.08, 0.09) | Synergistic |
| 1:5000 (1:2.5) | 0.27 (0.23, 0.31) | 0.31 (0.24, 0.38) | 0.35 (0.23, 0.48) | |
| 1:800 (2.5:1) | 0.15 (0.11, 0.19) | 0.31 (0.22, 0.40) | 0.65 (0.31, 0.98) | |
| *Tenofovir* | | | | |
| 1:40 (1:1) | 0.09 (0.07, 0.11) | 0.17 (0.12, 0.22) | 0.34 (0.18, 0.49) | Moderate-Synergistic |
| 1:100 (1:2.5) | 0.18 (0.13, 0.22) | 0.37 (0.23, 0.50) | 0.79 (0.30, 1.28) | |
| 1:16 (2.5:1) | 0.37 (0.31, 0.44) | 0.60 (0.46, 0.73) | 0.97 (0.62, 1.33) | |
| *Stavudine* | | | | |
| 1:600 (1:1) | 0.52 (0.40, 0.64) | 0.60 (0.41, 0.80) | 0.75 (0.36, 1.14) | Moderate-Synergistic |
| 1:1500 (1:2.5) | 0.38 (0.31, 0.45) | 0.37 (0.28, 0.46) | 0.40 (0.23, 0.56) | |
| 1:240 (2.5:1) | 0.69 (0.51, 0.88) | 0.78 (0.49, 1.07) | 0.92 (0.36, 1.48) | |
| *Zidovudine* | | | | |
| 1:6 (1:1) | 0.25 (0.17, 0.34) | 0.53 (0.29, 0.78) | 1.13 (0.24, 2.02) | Additive-Synergistic |
| 1:15 (1:2.5) | 0.46 (0.36, 0.56) | 0.52 (0.36, 0.68) | 0.59 (0.29, 0.89) | |
| 1:2.4 (2.5:1) | 0.37 (0.28, 0.47) | 0.49 (0.32, 0.67) | 0.66 (0.28, 1.05) | |
| *Lamivudine* | | | | |
| 1:80 (1:1) | 0.75 (0.45, 1.05) | 0.79 (0.35, 1.23) | 0.90 (0.11, 1.69) | Additive-Synergistic |
| 1:200 (1:2.5) | 0.13 (0.10, 0.16) | 0.21 (0.16, 0.27) | 0.39 (0.21, 0.58) | |
| 1:32 (2.5:1) | 0.14 (0.10, 0.17) | 0.26 (0.18, 0.33) | 0.49 (0.22, 0.75) | |
| *Abacavir* | | | | |
| 1:1000 (1:1) | 0.69 (0.49, 0.89) | 0.77 (0.46, 1.09) | 0.87 (0.30, 1.44) | Additive-Synergistic |
| 1:2500 (1:2.5) | 0.56 (0.45, 0.67) | 0.51 (0.37, 0.65) | 0.48 (0.27, 0.68) | |
| 1:400 (2.5:1) | 0.10 (0.05, 0.14) | 0.27 (0.16, 0.39) | 0.76 (0.14, 1.37) | |

[a] Ratio of Compound 1 to comparator compound.
[b] A lower bound of the asymptotic confidence interval greater than 1 indicates antagonism, an upper bound of less than 1 indicates synergism, and a value of 1 being contained in the interval indicates additivity. The 95% confidence intervals are shown in parenthesis, and represent a measure of variability in the data.

Two-Drug Combinations of Compound 1 with Non-Nucleoside Reverse Transcriptase Inhibitors. The results presented in Table 3 show that the combined effect of Compound 1 with efavirenz and delavirdine is synergistic while the effect with nevapiradine is additive-synergystic. No enhanced cytotoxicity was observed at the highest concentrations tested with any of the drug combinations.

TABLE 3

Two-Drug Combinations using Compound 1 and Non-Nucleoside Reverse Transcriptase Inhibitors.

| Molar Ratio | Combination Indices at % HIV Inhibition[b] (Confidence Interval) | | | Overall |
|---|---|---|---|---|
| (EC$_{50}$ Ratio)[a] | 50% | 75% | 90% | Result |
| Efavirenz | | | | |
| 1:2.5 (1:1) | 0.70 (0.50, 0.89) | 0.47 (0.30, 0.64) | 0.32 (0.13, 0.50) | Synergistic |
| 1:6.25 (1:2.5) | 0.47 (0.28, 0.65) | 0.46 (0.21, 0.70) | 0.45 (0.06, 0.83) | |
| 1:1 (2.5:1) | 0.52 (0.36, 0.69) | 0.39 (0.21, 0.57) | 0.30 (0.08, 0.51) | |
| Delavirdine | | | | |
| 1:8.33 (1:1) | 0.90 (0.75, 1.06) | 0.49 (0.38, 0.61) | 0.28 (0.18, 0.39) | Synergistic |
| 1:20.8 (1:2.5) | 0.57 (0.42, 0.71) | 0.55 (0.36, 0.75) | 0.57 (0.26, 0.89) | |
| 1:3.33 (2.5:1) | 0.64 (0.49, 0.78) | 0.46 (0.31, 0.60) | 0.34 (0.17, 0.50) | |
| Nevirapine | | | | |
| 1:150 (1:1) | 0.19 (0.15, 0.23) | 0.22 (0.16, 6.28) | 0.26 (0.15, 0.38) | Additive-Synergistic |
| 1:375 (1:2.5) | 0.48 (0.35, 0.62) | 0.66 (0.40, 0.92) | 0.92 (0.35, 1.49) | |
| 1:60 (2.5:1) | 0.58 (0.48, 0.67) | 0.99 (0.76, 1.22) | 1.71 (1.09, 2.33) | |

[a]Ratio of Compound 1 to comparator compound.
[b]A lower bound of the asymptotic confidence interval greater than 1 indicates antagonisms, an upper bound of less than 1 indicates synergism, and a value of 1 being contained in the interval indicates additivity. The 95% confidence intervals are shown in parenthesis, and represent a measure of variability in the data.

Two-Drug Combinations Involving Compound 1 and HIV Protease Inhibitors. In general, protease combinations with Compound 1 are synergistic to additive-synergistic. No cytotoxicity was observed at the highest concentrations used in any of these combination antiviral assays. Results from this two-drug combination study are summarized in Table 4.

TABLE 4

Two-Drug Combination using Compound 1 and Protease Inhibitors.

| Molar Ratio | Combination Indices at % HIV Inhibition[b] (Confidence Interval) | | | Overall |
|---|---|---|---|---|
| (EC$_{50}$ Ratio)[a] | 50% | 75% | 90% | Result |
| Ritonavir | | | | |
| 1:33.3 (1:1) | 0.60 (0.49, 0.72) | 0.61 (0.45, 0.77) | 0.70 (0.41, 0.99) | Synergistic |
| 1:83.3 (1:2.5) | 0.54 (0.45, 0.63) | 0.58 (0.44, 0.71) | 0.73 (0.46, 1.00) | |
| 1:13.3 (2.5:1) | 0.23 (0.20, 0.26) | 0.20 (0.17, 0.24) | 0.19 (0.14, 0.24) | |
| Saquinavir | | | | |
| 1:33.3 (1:1) | 0.31 (0.28, 0.33) | 0.31 (0.28, 0.35) | 0.32 (0.26, 0.38) | Synergistic |
| 1:83.3 (1:2.5) | 0.60 (0.52, 0.67) | 0.67 (0.56, 0.79) | 0.77 (0.56, 0.97) | |
| 1:13.3 (2.5:1) | 0.39 (0.33, 0.45) | 0.59 (0.46, 0.72) | 0.90 (0.58, 1.22) | |
| Atazanavir | | | | |
| 1:1 (1:1) | 0.53 (0.46, 0.60) | 0.67 (0.54, 0.79) | 0.90 (0.64, 1.17) | Additive-Synergistic |
| 1:2.5 (1:2.5) | 0.23 (0.16, 0.30) | 0.49 (0.29, 0.69) | 1.17 (0.38, 1.95) | |
| 1:0.4 (2.5:1) | 0.34 (0.26, 0.42) | 0.56 (0.38, 0.74) | 0.97 (0.46, 1.48) | |
| Lopinavir | | | | |
| 1:20 (1:1) | 0.47 (0.38, 0.56) | 0.66 (0.48, 0.84) | 1.02 (0.58, 1.46) | Additive-Synergistic |
| 1:50 (1:2.5) | 0.89 (0.73, 1.05) | 0.90 (0.67, 1.13) | 1.00 (0.60, 1.40) | |
| 1:8 (2.5:1) | 0.29 (0.25, 0.33) | 0.37 (0.30, 0.44) | 0.51 (0.37, 0.65) | |
| Nelfinavir | | | | |
| 1:6 (1:1) | 0.39 (0.34, 0.44) | 0.47 (0.39, 0.56) | 0.58 (0.41, 0.74) | Additive-Synergistic |
| 1:15 (1:2.5) | 0.41 (0.32, 0.50) | 0.81 (0.57, 1.05) | 1.61 (0.84, 2.37) | |
| 1:2.4 (2.5:1) | 0.12 (0.09, 0.15) | 0.32 (0.22, 0.42) | 0.87 (0.38, 1.35) | |

TABLE 4-continued

Two-Drug Combination using Compound 1 and Protease Inhibitors.

| Molar Ratio<br>($EC_{50}$ Ratio)[a] | Combination Indices at % HIV Inhibition[b] (Confidence Interval) | | | Overall Result |
|---|---|---|---|---|
| | 50% | 75% | 90% | |
| *Amprenavir* | | | | |
| 1:33.3 (1:1) | 0.14 (0.11, 0.17) | 0.35 (0.26, 0.45) | 0.87 (0.46, 1.28) | Additive- |
| 1:83.3 (1:2.5) | 0.13 (0.09, 0.17) | 0.27 (0.17, 0.38) | 0.58 (0.19, 0.97) | Synergistic |
| 1:13.3 (2.5:1) | 0.46 (0.32, 0.60) | 0.79 (0.46, 1.11) | 1.33 (0.42, 2.25) | |
| *Indinavir* | | | | |
| 1:20 (1:1) | 0.41 (0.26, 0.56) | 0.69 (0.34, 1.04) | 1.59 (0.29, 2.90) | Additive- |
| 1:50 (1:2.5) | 0.30 (0.18, 0.41) | 0.62 (0.32, 0.92) | 1.96 (0.29, 3.64) | Synergistic |
| 1:8 (2.5:1) | 0.05 (0.03, 0.06) | 0.16 (0.13, 0.20) | 0.68 (0.39, 0.98) | |

[a] Ratio of Compound 1 to comparator compound.
[b] A lower bound of the asymptotic confidence interval greater than 1 indicates antagonisms, an upper bound of less than 1 indicates synergism, and a value of 1 being contained in the interval indicates additivity. The 95% confidence intervals are shown in parenthesis, and represent a measure of variability in the data.

Two-Drug Combination of Compound 1 with Entry Inhibitors. The results presented in Table 5 indicate that the combination of Compound 1 with AMD-3100 is strongly synergistic at the 50 and 75% inhibition levels, with tendency to additivity at 90%. Therefore, it is classified as moderate synergistic. No significant cytotoxicity was observed at the highest concentration of the combined drugs.

TABLE 5

Anti-HIV Activity from a Two-Drug Combination using Compound 1 and Entry Inhibitors

| Molar Ratio<br>($EC_{50}$ Ratio)[a] | Combination Indices at % HIV Inhibition[b] (Confidence Interval) | | | Overall Result |
|---|---|---|---|---|
| | 50% | 75% | 90% | |
| *Enfuvirtide* | | | | |
| 1:10 (1:1) | 0.47 (0.40, 0.54) | 0.53 (0.42, 0.65) | 0.60 (0.39, 0.81) | Synergistic |
| 1:25 (1:2.5) | 0.48 (0.37, 0.60) | 0.60 (0.40, 0.80) | 0.75 (0.35, 1.15) | |
| 1:4 (2.5:1) | 0.35 (0.29, 0.40) | 0.47 (0.37, 0.57) | 0.63 (0.40, 0.86) | |
| *T-1249* | | | | |
| *AMD-3100* | | | | |
| 1:16 (1:1) | 0.44 (0.29, 0.60) | 0.62 (0.31, 0.92) | 0.98 (0.21, 1.76) | Moderate- |
| 1:40 (1:2.5) | 0.56 (0.42, 0.70) | 0.54 (0.35, 0.73) | 0.66 (0.29, 1.02) | Synergistic |
| 1:6.4 (2.5:1) | 0.52 (0.36, 0.68) | 0.61 (0.35, 0.88) | 0.77 (0.24, 1.31) | |
| *SchC* | | | | |
| 1:10 (1:1) | 0.19 (0.14, 0.25) | 0.46 (0.29, 0.63) | 1.12 (0.4, 1.83) | Additive- |
| 1:25 (1:2.5) | 0.50 (0.38, 0.61) | 0.92 (0.64, 1.21) | 1.74 (0.83, 2.65) | Synergistic |
| 1:4 (2.5:1) | 0.08 (0.05, 0.11) | 0.21 (0.14, 0.28) | 0.54 (0.21, 0.88) | |
| *SchD* | | | | |
| *UK-427,857* | | | | |

[a] Ratio of Compound 1 to comparator compound.
[b] A lower bound of the asymptotic confidence interval greater than 1 indicates antagonisms, an upper bound of less than 1 indicates synergism, and a value of 1 being contained in the interval indicates additivity. The 95% confidence intervals are shown in parenthesis, and represent a measure of variability in the data.

Two-Drug Combination of Compound 1 with an HIV integrase inhibitor. The results presented in Table 6 indicate that the combination of Compound 1 with Compound 2 is moderate synergistic. No significant cytotoxicity was observed at the highest concentration of the combined drugs.

TABLE 6

Anti-HIV Activity from a Two-Drug Combination using Compound 1 and Compound 2

| Molar Ratio ($EC_{50}$ Ratio)[a] | Combination Indices at % HIV Inhibition[b] (Confidence Interval) | | | Overall Result |
|---|---|---|---|---|
| | 50% | 75% | 90% | |
| | BMS-538203 | | | |
| 1:80 (1:1) | 0.48 (0.39, 0.58) | 0.51 (0.37, 0.65) | 0.54 (0.31, 0.76) | Moderate- |
| 1:200 (1:2.5) | 0.44 (0.36, 0.53) | 0.51 (0.37, 0.65) | 0.59 (0.34, 0.85) | Synergistic |
| 1:32 (2.5:1) | 0.50 (0.36, 0.63) | 0.70 (0.44, 0.97) | 1.00 (0.41, 1.59) | |

[a]Ratio of Compound 1 to comparator compound.

[b]A lower bound of the asymptotic confidence interval greater than 1 indicates antagonisms, an upper bound of less than 1 indicates synergism, and a value of 1 being contained in the interval indicates additivity. The 95% confidence intervals are shown in parenthesis, and represent a measure of variability in the data.

Pharmaceutical Composition and Methods of Use

Compound 1 inhibits HIV attachment, an essential step in HIV replication, and can be useful for the treatment of HIV infection and the consequent pathological conditions such as AIDS or ARC. As shown above, Compound 1 is active in conjunction with a wide variety of other agents and may be particularly beneficial in HAART and other new combination compositions and therapies.

Compound 1 will generally be given as a pharmaceutical composition, and the active ingredient of the composition may be comprised of Compound 1 alone or Compound 1 and at least one other agent used for treating AIDS or HIV infection. The compositions will generally be made with a pharmaceutically accepted carrier or vehicle, and may contain conventional excipients. The compositions are made using common formulation techniques. The invention encompasses all conventional forms. Solid and liquid compositions are preferred. Some solid forms include powders, tablets, capsules, and lozenges. Tablets include chewable, buffered, and extended release. Capsules include enteric coated and extended release capsules. Powders are for both oral use and reconstitution into solution. Powders include lyophilized and flash-melt powders. In a solid composition, Compound 1 and any antiretroviral agent are present in dosage unit ranges. Generally, Compound 1 will be in a unit dosage range of 1-1000 mg/unit. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquids include aqueous solutions, syrups, elixers, emulsions, and suspensions. In a liquid composition, Compound 1 and any antiretroviral agent are present in dosage unit ranges. Generally, Compound 1 will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral (injected intramuscular, intravenous, subcutaneous) methods are preferred. Generally, the dosing regimen will be similar to other antiretroviral agents used clinically. Typically, the daily dose will be 1-100 mg/kg body weight daily for Compound 1. Generally, more compound is required orally and less parenterally. The specific dosing regime, however, will be determined by a physician using sound medical judgement.

The invention also encompasses methods where Compound 1 is given in combination therapy. That is, Compound 1 can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, Compound 1 will generally be given in a daily dose of 1-100 mg/kg body weight daily in conjunction with other agents. The other agents generally will be given in the amounts used therapeutically. The specific dosing regime, however, will be determined by a physician using sound medical judgement.

Table 7 lists some agents useful in treating AIDS and HIV infection, which are suitable for this invention. The invention, however, is not limited to these agents.

TABLE 7

| DRUG NAME | MANUFACTURER | INDICATION |
|---|---|---|
| ANTIVIRALS | | |
| 097 (non-nucleoside reverse transcriptase inhibitor) | Hoechst/Bayer | HIV infection, AIDS, ARC |
| Amprenavir 141 W94 GW 141 (protease inhibitor) | Glaxo Wellcome | HIV infection, AIDS, ARC |
| Abacavir (1592U89) GW 1592 (RT inhibitor) | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection, ARC, |
| AL-721 | Ethigen (Los Angeles, CA) | PGL HIV positive, AIDS |
| Alpha Interferon HIV in combination w/Retrovir | Glaxo Wellcome | Kaposi's sarcoma |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) (protease inhibitor) | Bristol-Myers Squibb/ Novartis | HIV infection, AIDS, ARC |
| BMS-234475 (CGP-61755) (protease inhibitor) | Bristol-Myers Squibb/ Novartis | HIV infection, AIDS, ARC |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 (protease inhibitor) | AVID (Camden, NJ) | HIV infection, AIDS, ARC |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE (non-nucleoside RT inhibitor) | DuPont Merck | HIV infection, AIDS, ARC |

TABLE 7-continued

| DRUG NAME | MANUFACTURER | INDICATION |
|---|---|---|
| EL10 | Elan Corp, PLC (Gainesville, GA) | HIV infection |
| Famciclovir | Smith Kline | herpes zoster, herpes simplex |
| FTC (reverse transcriptase inhibitor) | Emory University | HIV infection, AIDS, ARC |
| GS 840 (reverse transcriptase inhibitor) | Gilead | HIV infection, AIDS, ARC |
| HBY097 (non-nucleoside reverse transcriptaseinhibitor) | Hoechst Marion Roussel | HIV infection, AIDS, ARC |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-associated diseases |
| Lamivudine, 3TC (reverse transcriptase inhibitor) | Glaxo Wellcome | HIV infection, AIDS, ARC, also with AZT |
| Lobucavir | Bristol-Myers Squibb | CMV infection |
| Nelfinavir (protease inhibitor) | Agouron Pharmaceuticals | HIV infection, AIDS, ARC |
| Nevirapine (RT inhibitor) | Boeheringer Ingleheim | HIV infection, AIDS, ARC |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 (protease inhibitor) | Pharmacia Upjohn | HIV infection, AIDS, ARC |
| Probucol | Vyrex | HIV infection, AIDS |
| RBC-CD4 | Sheffield Med. Tech (Houston, TX) | HIV infection, AIDS, ARC |
| Ritonavir (protease inhibitor) | Abbott | HIV infection, AIDS, ARC |
| Saquinavir (protease inhibitor) | Hoffmann-LaRoche | HIV infection, AIDS, ARC |
| Stavudine; d4T Didehydrodeoxy-thymidine | Bristol-Myers Squibb | HIV infection, AIDS, ARC |
| Valaciclovir | Glaxo Wellcome | Genital HSV & CMVinfections |
| Virazole Ribavirin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) (reverse transcriptase inhibitor) | Gilead | HIV infection, AIDS |
| Combivir ® (reverse transcriptase inhibitor) | GSK | HIV infection, AIDS |
| abacavir succinate (or Ziagen ®) (reverse transcriptase inhibitor) | GSK | HIV infection, AIDS |
| Reyataz ® (atazanavir) | Bristol-Myers Squibb | HIV infection, AIDS |

TABLE 7-continued

| DRUG NAME | MANUFACTURER | INDICATION |
|---|---|---|
| Fuzeon (Enfuvirtide, T-20) | Roche/Trimeris | HIV infection, AIDS, viral fusion inhibitor |
| Trizivir ® | | HIV infection, AIDS |
| Kaletra ® | Abbott | HIV infection, AIDS, ARC |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide Granulocyte Colony Stimulating Factor | Ciba-Geigy Corp. Amgen | Kaposi's sarcoma AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche in combination w/AZT | Kaposi's sarcoma, AIDS, ARC |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

TABLE 7-continued

| DRUG NAME | MANUFACTURER | INDICATION |
|---|---|---|
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

We claim:

1. A method for treating HIV infection in a human patient comprising administering a therapeutically effective amount of 1-benzoyl-4-[2-[4-methoxy-7-(3-methyl-1H-1,2,4-triazol-1-yl)-1H-pyrrolo[2,3-c]pyridin-3-yl]-1,2-dioxoethyl]-piperazine, or a pharmaceutically acceptable salt thereof, with a therapeutically effective amount of at least one other agent, including pharmaceutically acceptable salts thereof, used for treatment of AIDS or HIV infection selected from the group consisting of the nucleoside HIV reverse transcriptase inhibitors didanosine, emtricitabine and zalcitabine, the non-nucleoside HIV reverse transcriptase inhibitors delavirdine and efavirenz, the HIV protease inhibitors ritonavir and saquinavir, and the HIV fusion inhibitor enfuvirtide, wherein the $EC_{50}$ ratio of said piperazine compound to said other agent is 1:1, 1:2.5 or 2.5:1.

2. A pharmaceutical composition comprising a therapeutically effective amount of 1-benzoyl-4-[2-[4-methoxy-7-(3-methyl-1H-1,2,4-triazol-1-yl)-1H-pyrrolo[2,3-c]pyridin-3-yl]-1,2-dioxoethyl]-piperazine, or a pharmaceutically acceptable salt thereof, with at least one other agent, including pharmaceutically acceptable salts thereof, used for treatment of AIDS or HIV infection selected from the group consisting of the nucleoside HIV reverse transcriptase inhibitors didanosine, emtricitabine and zalcitabine, the non-nucleoside HIV reverse transcriptase inhibitors delavirdine and efavirenz, the HIV protease inhibitors ritonavir and saquinavir, and the HIV fusion inhibitor enfuvirtide, and a pharmaceutically acceptable carrier, wherein the $EC_{50}$ ratio of said piperazine compound to said other AIDS or HIV agent is 1:1, 1:2.5 or 2.5:1.

* * * * *